(12) United States Patent
Young (10) Patent No.: US 9,044,218 B2
(45) Date of Patent: Jun. 2, 2015

(54) DISTRACTOR

(75) Inventor: Duncan Young, Beeston (GB)

(73) Assignee: DEPUY (IRELAND), Cork (IE)

( * ) Notice: Subject to any disclaimer, the term of this patent is extended or adjusted under 35 U.S.C. 154(b) by 324 days.

(21) Appl. No.: 13/640,338

(22) PCT Filed: Mar. 18, 2011

(86) PCT No.: PCT/GB2011/050540
§ 371 (c)(1), (2), (4) Date: Nov. 29, 2012

(87) PCT Pub. No.: WO2011/128657
PCT Pub. Date: Oct. 20, 2011

(65) Prior Publication Data
US 2013/0138112 A1 May 30, 2013

(30) Foreign Application Priority Data
Apr. 14, 2010 (GB) .................................. 1006173.7

(51) Int. Cl.
*A61B 17/58* (2006.01)
*A61B 17/60* (2006.01)
*A61F 2/00* (2006.01)
*A61B 17/02* (2006.01)
*A61B 17/00* (2006.01)

(52) U.S. Cl.
CPC ..... *A61B 17/025* (2013.01); *A61B 2017/00991* (2013.01); *A61B 2017/0268* (2013.01)

(58) Field of Classification Search
CPC ...................... A61B 17/025; A61B 2017/0268

USPC .................................. 606/90, 105; 623/17.15
See application file for complete search history.

(56) References Cited

U.S. PATENT DOCUMENTS

| 5,733,292 A | 3/1998 | Gustilo |
| 5,989,290 A | 11/1999 | Biedermann |
| 8,303,663 B2 * | 11/2012 | Jimenez et al. ............ 623/17.16 |
| 2004/0172129 A1 | 9/2004 | Schafer |
| 2007/0233144 A1 | 10/2007 | Lavallee |
| 2008/0114367 A1 | 5/2008 | Meyer |
| 2009/0222089 A1 | 9/2009 | Hauri |

FOREIGN PATENT DOCUMENTS

WO    2008021972 A2    2/2008

OTHER PUBLICATIONS

PCT International Search Report PCT/GB2011/050540 dated Jul. 4, 2011.
UK Search Report GB1006173.7 dated Aug. 12, 2010.

* cited by examiner

*Primary Examiner* — Andrew Yang (57) ABSTRACT

A surgical distractor comprising a base plate (2), an intermediate stage (6) telescopically coupled to the base plate (2) and a distraction plate (4) telescopically coupled to the intermediate stage (6). The intermediate stage (6) is arranged to rotate relative to at least one of the base plate (2) and the distraction plate (4) to cause telescopic movement between the intermediate plate (6) and at least one of the base plate (2) and the distraction plate (4) such that the distraction plate (4) moves towards or away from the base plate (2). Surgical instrument kits incorporating distractors and drive elements and a method of distracting two bones within a joint are also disclosed.

10 Claims, 6 Drawing Sheets

FIG. 9 ured. An adjustable distractor in accordance with an
DISTRACTOR

CROSS REFERENCE TO RELATED APPLICATION

This application is a National Stage 35 U.S.C. 371 of International Patent Application PCT/GB2011/050540 filed Mar. 18, 2011.

BACKGROUND OF THE INVENTION

The present invention relates to a distractor. Particular embodiments of the present invention relate to a surgical distractor for use in orthopaedic surgery to move apart bones within a joint. The present invention also relates to methods of using a surgical distractor.

During the lifetime of a patient, it may be necessary to perform a joint replacement procedure on the patient as a result of, for example, disease or trauma. The joint replacement procedure, or joint arthroplasty, may involve the use of a prosthesis which is implanted into one or more of the patient's bones. During a joint replacement procedure it may be necessary to assess the size of the natural gap between the bones of the joint, or to assess the size of a gap formed when portions of the bones within the joint are resected. Furthermore, it may be necessary to measure or assess the tension within soft tissue surrounding the joint for given sizes of gap created and maintained between the bones. Embodiments of the present invention relate to surgical instruments for generating and maintaining gaps between bones of a joint prior to the final implantation of the prosthetic joint.

BRIEF SUMMARY OF THE INVENTION

An example of a surgical procedure in which it is necessary to form and maintain a gap between bones is a knee replacement procedure. A surgical instrument set for performing a knee replacement procedure is marketed by DePuy Orthopaedics, Inc. under the trade mark Sigma High Performance Instruments.

For implanting a femoral prosthesis using the Sigma HP instrument set, it is first necessary to perform a resection of the distal tip of the femur forming a transverse resected surface to support a femoral prosthesis sizing guide. Similarly, the proximal end of the tibia is resected to create more room in the joint space and to receive a tibial component of the knee prosthesis. Once the femur and the tibia have been resected, the knee is placed in full extension. Laminar spreaders are applied medially and laterally to open up the joint space. The extension gap is preferably rectangular when the knee is fully extended.

The Sigma HP instrument set comprises a set of spacer blocks to measure the joint space. The spacer blocks are available in two options corresponding to fixed tibial implants and tibial implants having mobile bearing surfaces. Each spacer block comprises a bar with blocks at each end generally shaped in cross section to fit the joint space. The height of the block at each end differs. The thicker end is used for measuring the joint space when the knee is in extension. The thinner end is used for measuring the joint space when the knee is in flexion. The extension gap side of the spacer block is used to determine the appropriate thickness of the tibial insert and to validate the soft tissue balance. The bar includes a series of holes to receive an alignment rod. The knee is extended and the extension gap spacer block is positioned in the joint space the alignment rod should extend parallel to the longitudinal axis of the lower leg. The spacer block that best fits the available joint space indicates the required size of tibial implant.

U.S. Pat. No. 5,733,292 discloses an adjustable trial prosthesis for assessing the functioning of a knee joint without having to repeatedly remove and replace trial prostheses. The adjustable trial prosthesis comprises a first surface which recreates the top surface of the permanent prosthesis (which bears against the femoral prosthesis) and a second surface to engage the tibia. A distance adjustment mechanism is arranged to alter the distance between the first and second surfaces. In one embodiment the distance adjustment mechanism comprises a threaded bar with a nut coupled to the upper surface to adjust the position of the surface along the bar. The threaded bar extends through the second surface into a bore extending into the tibia. A lever is used to rotate the bar to adjust the position of the second surface along the bar to variably space apart the first and second surfaces.

While the spacer blocks described above can accurately fit that knee joint space, a large number of spacer blocks are required for variation in the joint space across a population. The adjustable trial prosthesis of U.S. Pat. No. 5,733,292 requires a bore extending into a bone in order to accommodate the threaded bar. There is a need for a surgical distractor suitable, for instance for use in a knee joint space, that can vary in thickness to determine the size of the joint space.

It is an object of embodiments of the present invention to obviate or mitigate one or more of the problems associated with the prior art, whether identified herein or elsewhere.

According to a first aspect of the present invention there is provided a surgical distractor comprising: a base plate; an intermediate stage telescopically coupled to the base plate; and a distraction plate telescopically coupled to the intermediate stage; wherein the intermediate stage is arranged to rotate relative to at least one of the base plate and the distraction plate to cause telescopic movement between the intermediate plate and at least one of the base plate and the distraction plate such that the distraction plate moves towards or away from the base plate.

An advantage of the present invention is that the distractor is compact. When the base plate and the distraction plate are at their closest positions, the distraction mechanism is entirely contained between the plates. This is particularly advantageous if the distractor is used in combination with a sensor for detecting force within the joint as if the mechanism extends from the joint space then this would adjust the force measurement. Furthermore, it is particularly advantageous that the distractor is entirely contained within a knee joint space because this allows the knee joint including the patella to be reduced so that the joint balance can be assessed with the knee's natural extensor mechanism operating normally. If the patella has to remain everted when the knee joint is reduced owing to a distractor which extends outside of the knee space then the assessment of knee balance is necessarily compromised. An adjustable distractor in accordance with an embodiment of the present invention allows a surgeon to determine the compromise between joint space and tension more quickly and easily than is possible with a static distractor such as a spacer block.

While the distractor is compact, the telescopic mechanism allows for a large expansion ratio. For instance, embodiments of the present invention may be approximately 4 mm-6 mm thick when compressed, but telescope to 12 mm-24 mm when fully expanded. For instance, embodiments of the invention may expand from 4 mm to around 10 mm or from around 6 mm to around 17 mm.

There may be two separate distraction mechanisms coupled to the same base plate. Specifically there may be two distraction plates coupled to a single base plate each by one or more intermediate stages. The separate distraction mechanisms may be driven one at a time or in tandem.

Each telescopic coupling may be generally circular and comprises helical structures formed upon the intermediate stage and the base plate or the distraction plate which convert relative rotary movement between the intermediate stage and the base plate or the distraction plate into relative linear movement between the intermediate stage and the base plate or the distraction plate along the axis of rotation.

Each telescopic coupling may comprise three helical structures such that each of the base plate and the intermediate stage and the intermediate stage and the distraction plate are coupled together at three points spaced apart around the circumference of each telescopic coupling.

The pitch of each helical structure for each telescopic coupling is the same.

The surgical distractor may further comprise one or more further intermediate stages telescopically coupled between the first intermediate stage and the distraction plate.

Each telescopic coupling may comprise a threaded coupling. Alternatively, each telescopic coupling may comprise at least one inclined slot formed in a first component and at least one pin extending from a second component to be received within the slot and to slide along the slot.

The distraction plate may further comprise a post extending towards the base plate and at least one intermediate stage is ring shaped, extends round the post and is arranged to rotate around the post so that the intermediate stage moves towards or away from the distraction plate.

An intermediate stage may be received within a bore formed in the base plate and arranged to rotate within the bore such that the intermediate stage moves towards or away from the base plate.

The distraction plate may be arranged to rotate relative to the base plate to cause telescopic movement.

According to a second aspect of the present invention there is provided a surgical instrument kit comprising: a surgical distractor as described above, wherein the distraction plate comprises a knurled rim and the surgical distractor further comprises an axle hole formed in the base plate; and an adjustment drive shaft having a tip to be received within the axle hole and a splined shaft proximal to the tip arranged to engage the knurled rim of the distraction plate when the tip is inserted into the axle hole; wherein rotating the drive shaft when the tip is received within the axle hole rotates the distraction plate relative to the base plate causing the distraction plate to move towards or away from the base plate.

The surgical distractor may further comprise a drive ring received within a bore formed in the base plate and arranged to rotate within the bore without causing axial movement of the drive ring, wherein an intermediate stage is received within the drive ring and arranged to rotate within the drive ring bore such that the intermediate stage moves towards or away from the base plate.

The drive ring may be arranged to rotate relative to the base plate while the distraction plate remains in a fixed angular position relative to the base plate to cause telescopic movement.

The distraction plate is prevented from rotating relative to the base plate by a locking tab engaging a channel within the base plate.

According to a third aspect of the present invention there is provided a surgical instrument kit comprising: a surgical distractor as described above, wherein the drive ring comprises a gear ring and the surgical distractor further comprises a worm gear extending through a bore within the base plate and engaging the gear ring such that rotating the worm gear about a first axis causes the drive ring to rotate about a second axis transverse to the first axis; and an adjustment drive shaft arranged to engage the worm gear such that rotating the drive shaft causes the drive ring to rotate relative to the base plate and the distraction plate to move towards or away from the base plate.

The worm gear may be connected to a rod having a spur gear at an opposite end, the surgical distractor further comprises an axle hole formed in the base plate; wherein the drive shaft has a tip to be received within the axle hole and a splined shaft proximal to the tip arranged to engage the spur gear when the tip is inserted into the axle hole; and wherein rotating the drive shaft when the tip is received within the axle hole rotates the spur gear causing the drive ring to rotate relative to the base plate and the distraction plate to move towards or away from the base plate

BRIEF DESCRIPTION OF THE DRAWINGS

According to a fourth aspect of the present invention there is provided a method of distracting two bones within a joint, the method comprising: forming a joint space between the bones; inserting a surgical distractor into the joint space, the surgical distractor comprising: a base plate; an intermediate stage telescopically coupled to the base plate; and a distraction plate telescopically coupled to the intermediate stage; the method further comprising: rotating the intermediate stage relative to at least one of the base plate and the distraction plate causing telescopic movement between the intermediate plate and at least one of the base plate and the distraction plate such that the distraction plate moves away from the base plate to distract the bones.

Embodiments of the present invention will now be described, by way of example only, with reference to the accompany drawings, in which.

DETAILED DESCRIPTION OF THE INVENTION

Embodiments of the present invention relate to surgical distractors. The distractors are generally applicable to surgical procedures where it is necessary to distract a gap between tissues. In particular, the distractors are suitable for distracting a gap between bones and so are particularly useful within orthopaedic procedures. One particular application is for determining the size of a joint space within a knee joint as discussed above.

Figure 1:
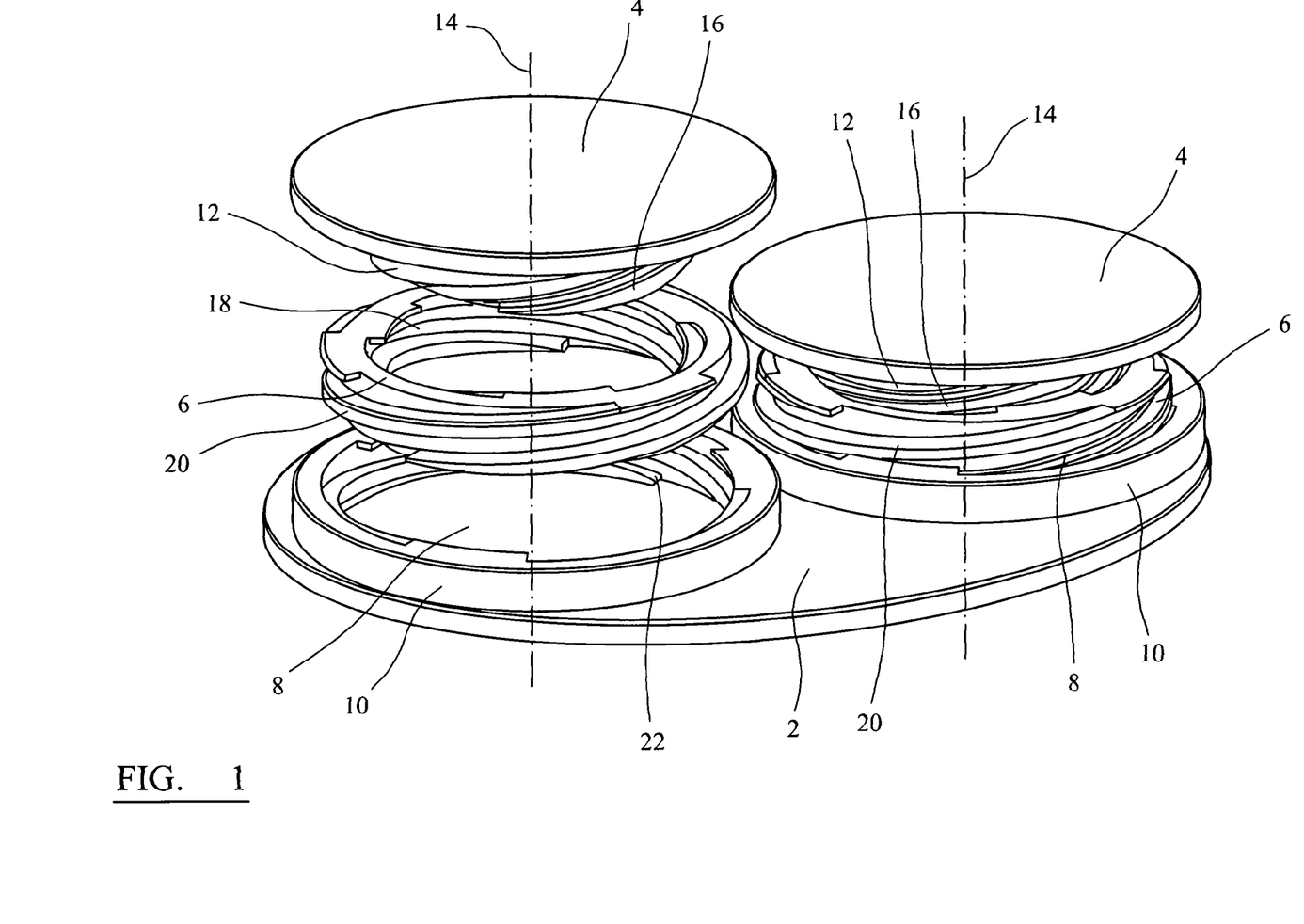
FIG. 1 illustrates a perspective and partially exploded view of a surgical distractor in accordance with a first embodiment of the present invention.

Referring first to FIG. 1, this illustrates a distractor in accordance with a first embodiment of the present invention for distracting a gap within a knee joint. The distractor comprises a pair of distraction mechanisms. It will be appreciated that in other embodiments of the present invention there may be a different number of distraction mechanisms according to the relative size of bones or other tissues to be distracted.

The distractor comprises a base plate 2 and first and second distraction plates 4. Each distraction mechanism comprises the coupling between the base plate 2 and a respective distraction plate 4. Two distraction mechanisms are provided in the embodiment of FIG. 1 such that the base plate 2 can be positioned upon a resected surface at the proximal end of a tibia and each distraction plate can separately engage a respective femoral condyle to allow for independent distraction between each condyle and the tibia. The separate distraction mechanisms may be operated independently of one another to allow for an asymmetric joint space if required, for instance to accommodate a knee joint where one condyle is more worn than the other. Both distraction mechanisms may be driven at the same time to adjust the heights of the distraction plates symmetrically. Alternatively, the distraction mechanisms may be separately driven, or it may only be possible to only drive one distraction mechanism at a time.

FIG. 1 illustrates the left hand distraction mechanism in an exploded view to make internal features visible. Coupled between the base plate 2 and each distraction plate 4 is an intermediate stage 6. In the embodiment of FIG. 1 each intermediate stage 6 comprises a ring arranged to be received in a bore 8 within an annular raised portion 10 of the base plate 2. Each distraction plate 4 is coupled to its respective intermediate stage 6 via a post 12 which extends downwardly from the plate. When assembled, post 12 is received within the ring of the intermediate stage 6, which in turn is received in bore 8 in base plate 2. The post 12, intermediate stage 6 and bore 8 for each distraction mechanism are defined by concentric circles about a common axis 14.

Post 12 further comprises an exterior screw thread 16 which couples to a corresponding internal screw thread 18 within the intermediate stage 6. Similarly, the exterior of the intermediate stage 6 comprises an external screw thread 20 which couples to a corresponding internal screw thread 22 within the bore 8. Rotating a distraction plate 4 while the base plate 2 is held steady (for instance by friction acting against the tibia) causes either threads 16 and 18 to slide relative to one another or threads 20 and 22 to slide relative to one another, or both according to respective frictional forces within the distraction mechanism.

Preferably both sets of screw threads are left handed or both are right handed such that rotating a distraction surface 4 relative to the base plate 2 causes the distraction plate 4 to move towards or away from the base plate 2. The movement is telescopic. Specifically, the post 12 telescopes from the bore within the intermediate stage 6 and/or the intermediate stage 6 telescopes from bore 8 within base plate 2. Relative axial movement between the distraction plates 4 and the base plate 2 is limited at one extent of travel by the underside of the distraction plate 4 coming to rest against the upper edge of annular raised portion 10. At the other extent of travel further axial movement is limited when both sets of screw threads are unscrewed almost to the point of disassembling the distraction mechanism.

Preferably, the pitch of each screw thread is identical. Advantageously this means that as the distraction plate 4 rotates relative to the base plate 2 it is irrelevant which external screw thread slides through its respective internal screw thread first. The angular position of the distraction plate 4 relative to the base plate 2 is therefore directly indicative of the height of the distraction plate 4 above the base plate 2 regardless of which part of the two stage telescope mechanism has moved first. A gauge may be provided around the circumference of the distraction plate 4 to indicate the height of the distraction mechanism to the surgeon. Preferably the pitch angle and the lengths of each internal screw thread are chosen such that full axial movement of the distraction plate relative to the base plate corresponds at most to only a single rotation of the distraction plate 4 so that the gauge may be read unambiguously.

The thread pitch angle is constant on each stage, which results in no change in mechanical advantage as the distractor expands so the surgeon can have some tactile feedback relating to the distraction force applied when they rotate the distraction plate. This is in contrast, for instance, to a screw jack system where the mechanical advantage varies as the mechanism expands. Advantageously, the forces within the distraction mechanisms are primarily shear and compressive, not bending forces (as would be the case for any distraction mechanism employing a lever). Therefore, dynamic inaccuracies in the distraction measurement (that is, the height of the distraction plate above the base plate for a given rotational position) are minimised and peak stresses may be reduced, allowing the use of disposable materials and thinner wall sections in reusable materials.

Preferably, the pitch angle of each screw thread is relatively shallow such that as pressure is applied across the distraction mechanism, for instance within a knee joint, this does not cause back drive of the mechanism. For instance, for each distraction stage the screw pitch may be 8 mm per turn. Preferably, each screw thread is a triple start screw thread. This ensures that each the distraction plate 4 is supported at each screw thread by three contact points within the screw thread. Advantageously, this ensures the stability of each distraction plate 4 such that when inserted into a knee space the distractor is not affected by movement within the knee and functions as a solid block for transferring load, for instance to a force sensor. In this respect, distractors in accordance with embodiments of the present invention may be directly substituted in place of spacer blocks. Advantageously, only a single distractor may be required in place of a large number of different sizes of spacer blocks, thereby reducing the size and complexity of the instrument set. Furthermore, unlike a set of spacer blocks, distractor mechanisms in accordance with embodiments of the present invention may be adjusted in height while remaining within the joint, increasing the speed and ease of determining the compromise between joint space and tension. The surgeon can readily optimise the size of the joint space for the final prosthetic implant versus tension and biomechanical performance of the joint.

The distraction mechanisms forming the distractor of FIG. 1 are two stage distraction mechanisms as there are two threaded couplings between the plates and the intermediate stage. Advantageously, when the distractor is fully collapsed, the screw threads overlap and are entirely contained within bore 8. When fully distracted the screw threads telescope from one another. This allows for a large range of movement of the distraction plate. It will be appreciated that there may be more intermediate stages, resulting in a larger range of movement. The principle limit on the number of stages is the manufacturing technique adopted, for instance limits on the minimum wall thickness of components.

The distractor of FIG. 1 may be intended for use as a single use surgical instrument. Consequently, the base plate, distraction plates and intermediate stages may be moulded components, for instance formed from a plastics material. The shape of the screw threads is chosen to be readily reproducible by moulding. Specifically, each screw stage is designed to be reproducible with open-and-shut tooling so that the distractor can be delivered as an injection moulded low cost single use device. However, certain embodiments of the present invention are suitable for use as reusable instruments and so differing construction techniques may be used and different materials may be used, along with different designs of the telescoping coupling between the stages. For instance the distractors may be machined from stainless steel.

Figure 2:
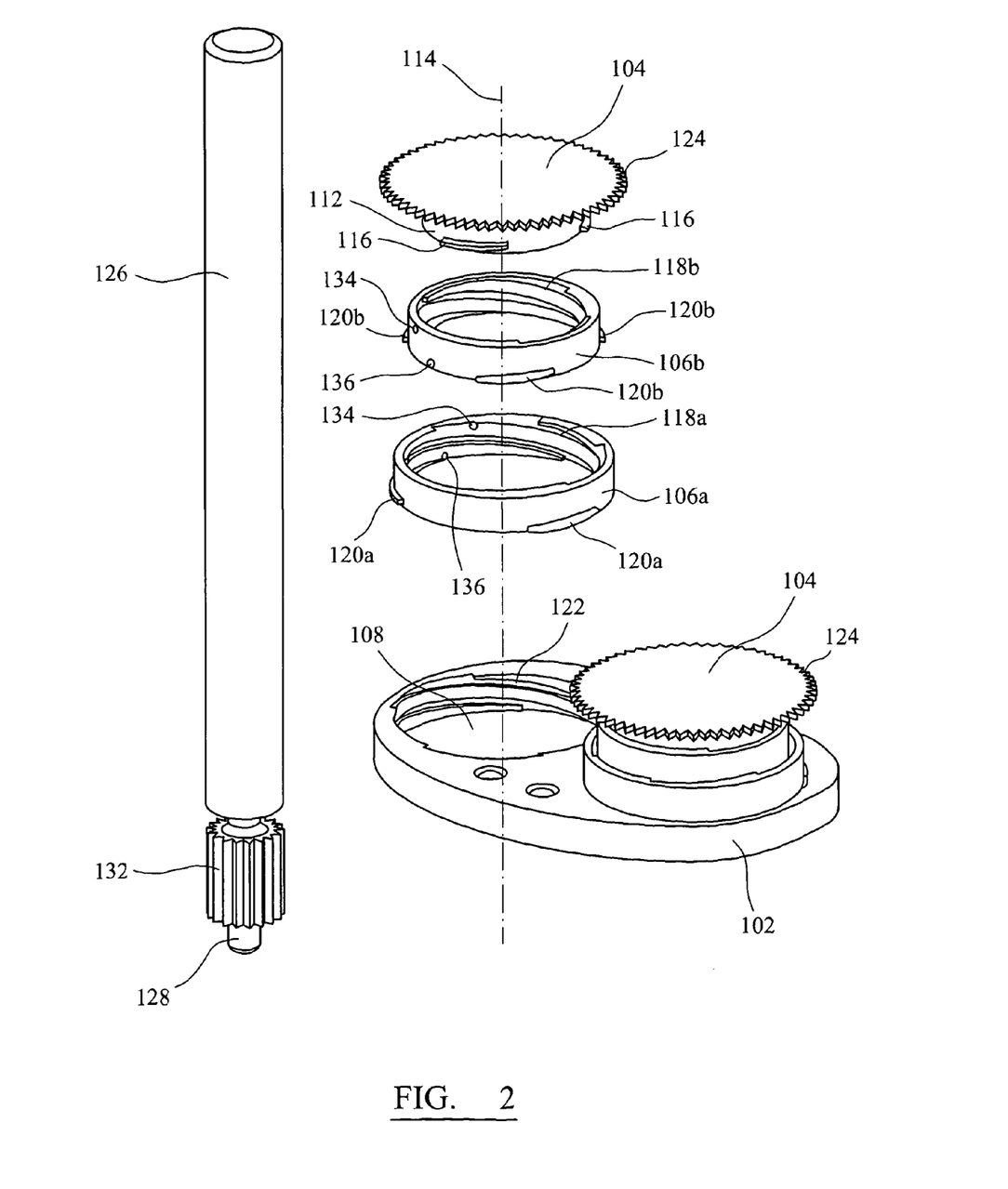
FIG. 2 illustrates a perspective and partially exploded view of a surgical distractor in accordance with a second embodiment of the present invention in combination with an adjustment drive shaft.
Figures 3, 4:
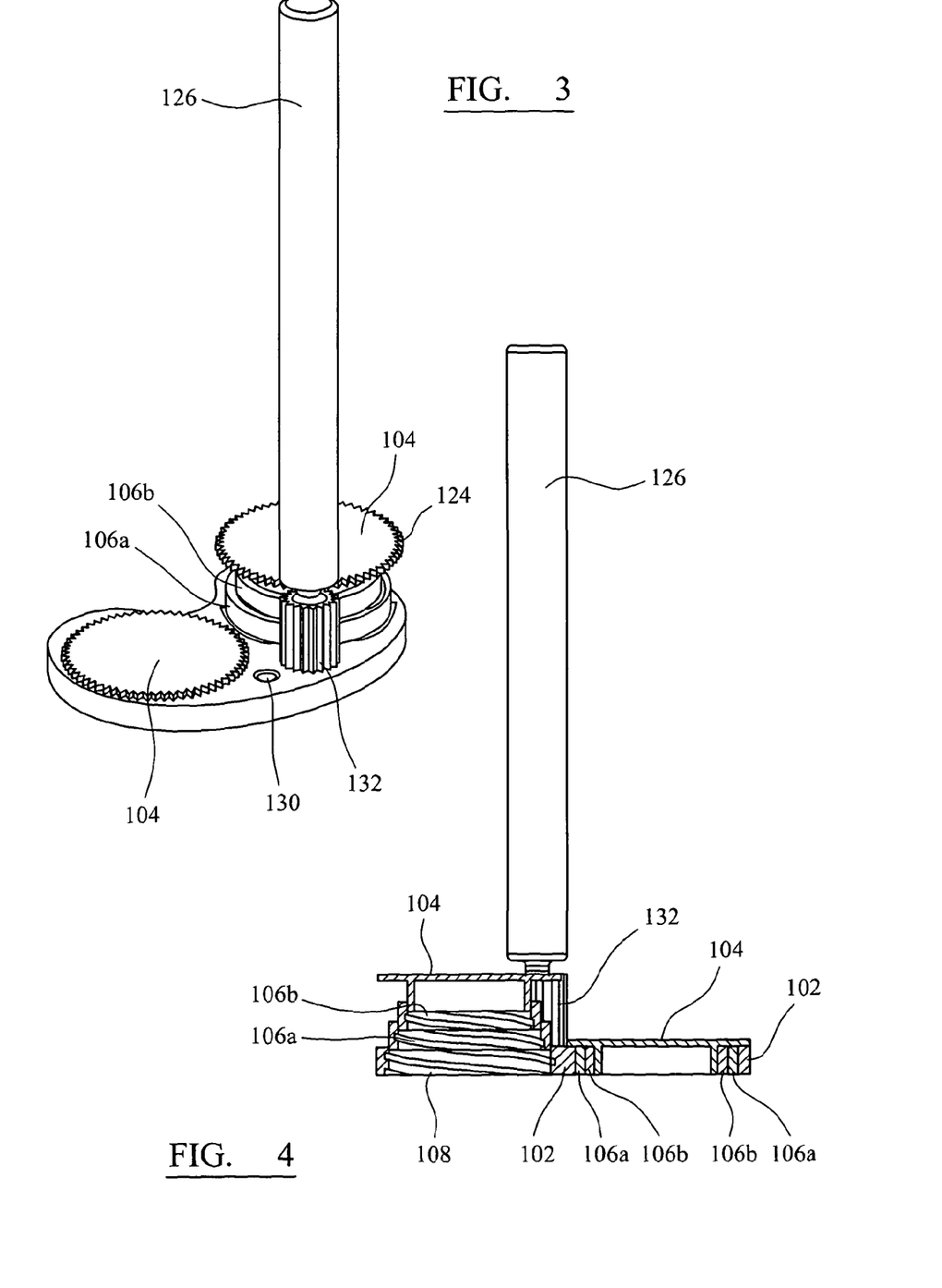
FIG. 3 illustrates a perspective view of the surgical distractor of FIG. 2 driven by the adjustment drive shaft.
FIG. 4 illustrates a cross sectional view of the surgical distractor of FIG. 2.

The distractor of FIG. 1 comprises distraction plates 4 which are turned by hand in order to adjust the gap between the distraction plates 4 and the base plate. FIGS. 2 to 5 illustrate a distractor in accordance with a second embodiment which includes a drive mechanism allowing the distraction plates to be driven to cause them to rotate and thereby adjust in height relative to the base plate. FIG. 2 illustrates a perspective and partially exploded view of the second embodiment of the surgical distractor in combination with a drive shaft. FIG. 3 illustrates an assembled perspective view of the surgical distractor of FIG. 2 driven by the drive shaft with one distraction mechanism in its extended state. FIG. 4 illustrates a cross sectional view of the surgical distractor of FIGS. 2 and 3. The distractor of FIGS. 2 to 4 is similar to the distractor of FIG. 1. Therefore, corresponding features are identified by the reference numbers which are incremented by 100.

The distractor of FIGS. 2 to 4 again comprises two distraction mechanisms between a base plate 102 and respective distraction plates 104. However, whereas the distractor of FIG. 1 comprises two stage distraction mechanisms, the distractor of FIGS. 2 to 5 comprises three stage distraction mechanisms. Specifically, the distraction mechanisms comprise two intermediate stages, an outer intermediate stage 106a and an inner intermediate stage 106b. When assembled, the distraction plate post 112, the intermediate stages 106a, 106b and the base plate bore 108 are nested together with the screw threads extending about a common axis 114. The internal screw threads 122, 118a, 118b and 122 are generally similar to the internal screw threads of FIG. 1. However, the external screw threads 120a, 120b and 116 each comprise three short screw threads. Advantageously, the short threads reduce friction within the distraction mechanisms. Additionally, the short external threads assist in allowing the maximum possible expansion of the distraction mechanisms before the threads engage stop pins to prevent the mechanism disassembling, as discussed below.

For the distractors of FIGS. 2 to 4, each distraction plate 104 has a knurled rim 124 forming a gear wheel with a 0.5 MOD profile to form part of a drive mechanism. Additionally, the knurled rim assists a surgeon who chooses to manually rotate the distraction plates 104. The knurled rim is intended to be driven by an adjustment drive shaft 126. The drive shaft 126 comprises a cylindrical tip 128 arranged to be received within a respective axle hole 130 for driving each distraction mechanism. As shown best in FIG. 2, adjacent to the cylindrical tip 128 the drive shaft 126 comprises a splined shaft 132. The splined shaft 132 engages the knurled rim 124 of an adjacent distraction plate 104 such that rotating the drive shaft 126 drives the rotation of the distraction plate 104. The holes 130 are positioned to allow drive shaft access through the intercondylar gap, generally parallel to the femur when the knee is in extension, such that the distractor can be driven when in position within the knee joint.

In order to prevent the disassembly of the distraction mechanisms, locking pins are inserted through holes 134 in the walls of the base plate 102 and the intermediate stages 106a, 106b (best seen in FIG. 2). The pins are arranged to extend through the grooves of the internal screw threads 122, 118a, and 118b in order to limit the travel of the external screw threads 120a, 120b as the distraction mechanisms expand, thereby preventing the distraction plate 104 and the intermediate stages from being disassembled by excessively rotating the distraction plate 104. The external threads are very short allowing them to be stopped at full extension. At least one pin is required for each internal telescopic stage, however more pins may be provided for each stage, for instance one for each external screw thread. Further pins may be inserted through the wall of base plate 102 in order to limit the extent of travel of the outer intermediate stage 106a as the distraction mechanism is collapsed. The collapsed position of the distraction plate 104 is limited by the underside of the plate contacting the upper edge of either intermediate stage 106a, 106b. Further pins may be inserted through holes 136 in the walls of the outer intermediate stages 106a, 106b to limit the collapsed position of the inner intermediate stage. Pins must be inserted through each hole 136 before the next outer stage is coupled otherwise pin holes 136 are covered.

The three stage telescopic mechanism of FIGS. 2 to 4 may be provided as a machined metal reusable device with a minimum wall section of approximately 1 mm. A single use version formed from a plastic material may be formed with a 1.5 mm wall section with two stages in similar package size.

Figure 5:
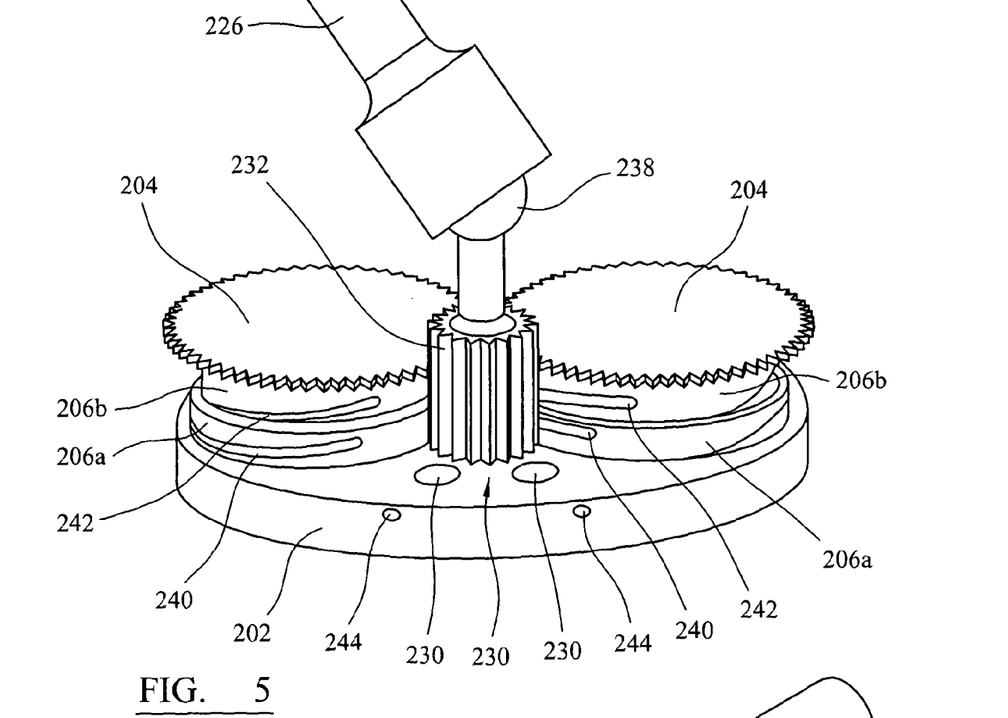
FIG. 5 illustrates a perspective view of a surgical distractor in accordance with a third embodiment of the present invention in combination with an adjustment drive shaft.

FIG. 5 illustrates a distractor in accordance with a third embodiment. The third embodiment is generally similar to the second embodiment and corresponding features are identified by reference signs which have been incremented by 100.

For the distractor of FIG. 5, a third axle hole 230 (not visible due to the drive shaft 226) is provided between the pair of axle holes 230 which correspond to those of FIGS. 2 to 5. The third axle hole 230 is intermediate of the distraction plates 204 such that both plates may be driven simultaneously by the splined shaft 232 of drive shaft 226. The drive shaft 226 is provided with a universal joint 238 to make it easier to drive the distractor when position in a knee joint.

The distractor of FIG. 5 also differs from the distractor of FIGS. 2 to 4 in that in place of screw threads each intermediate stage 206a, 206b comprises inclined slots 240, 242. Each intermediate stage 206a, 206b comprises three inclined slots 240, 242 which extend around the intermediate stages 206a, 206b at a similar pitch to the screw threads of the distractor of FIGS. 1 to 4. Pins are passed through holes 244 in base plate 202 to be received in each slot 240 (one pin for each slot 240, 242 spaced apart around the base plate 202). The pins ride within the slots 240 such that as the intermediate stage 206a rotates relative to the base plate 202 the intermediate stage 206a telescopes from the base plate. The ends of the slots 240 limit the extent of travel of the intermediate stage 206a. Similarly, pins pass through the walls of outer intermediate stages 206a to engage slots 242 upon the inner intermediate stages 206b. Although not visible in FIG. 6, the posts 212 on the underside of distraction plates 204 are provided with inclined slots to receive pins passing through the walls of the inner intermediate stages 206b. The pins and inclined slots are functionally equivalent to the short external screw threads of FIGS. 2 to 4 and provide the same stable support at three points spaced around the circumference of the telescopic stages.

Figure 6:
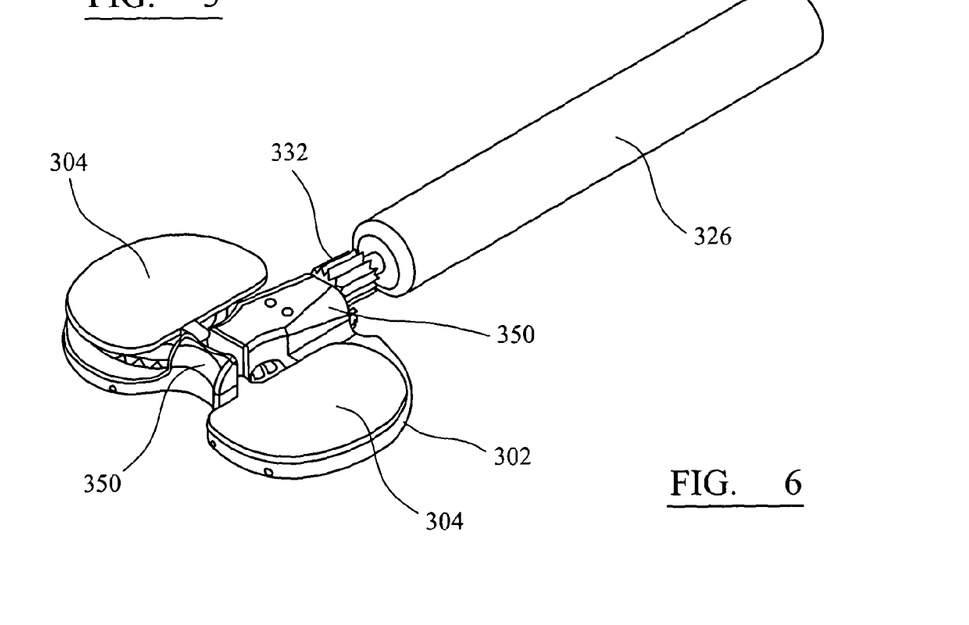
FIG. 6 illustrates a perspective view of a surgical distractor in accordance with a fourth embodiment of the present invention being driven by an adjustment drive shaft.
Figure 7:
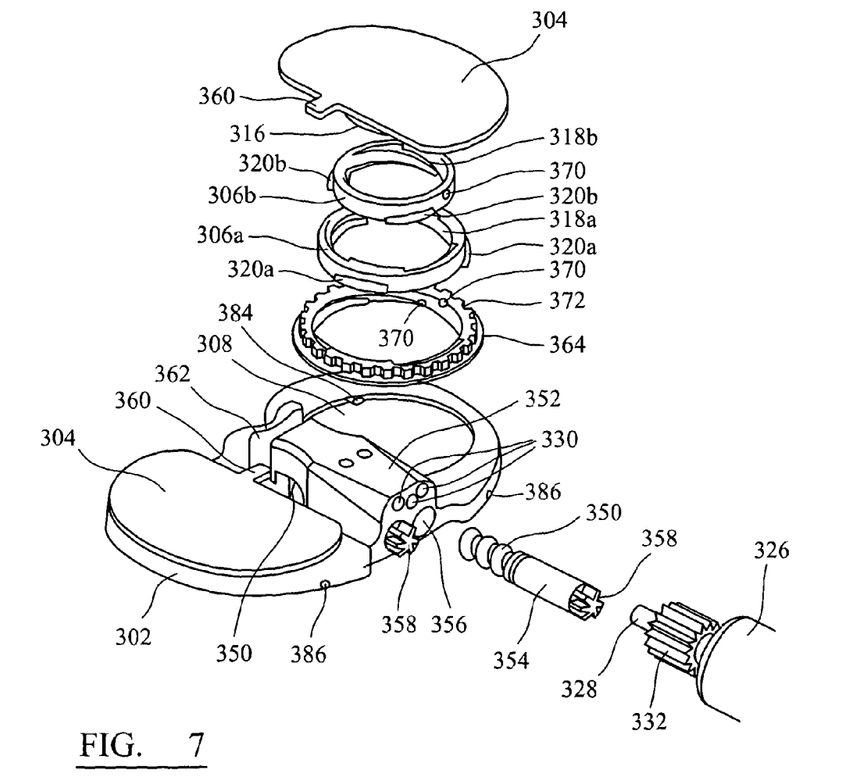
FIG. 7 illustrates a perspective and partially exploded view of the surgical distractor of FIG. 6.
Figure 8:
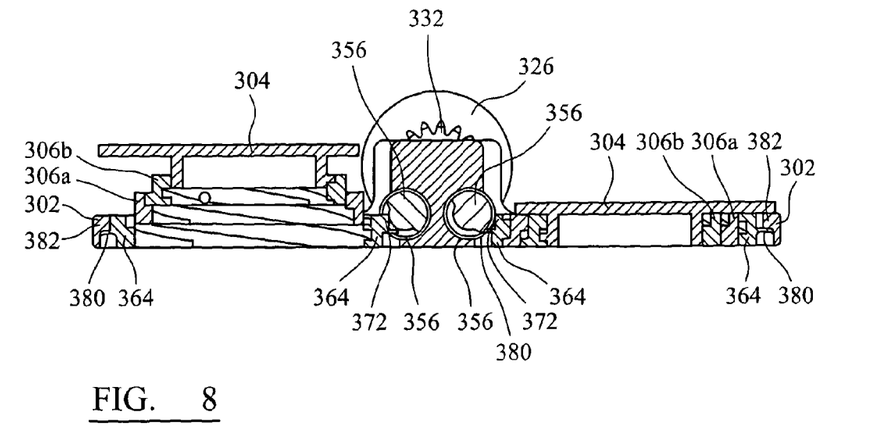
FIG. 8 illustrates a cross sectional view of the surgical distractor of FIG. 6.

Referring now to FIGS. 6 to 8, these illustrate a perspective view, a partially exploded perspective view and a cross sectional view of a surgical distractor in accordance with a fourth embodiment of the present invention in combination with an adjustment drive shaft. Features which correspond to those of FIG. 5 are indicated by reference numbers which are incremented by 100.

The distractor of the fourth embodiment of the invention differs from the preceding embodiments in that the distraction plates 304 do not rotate as the distraction mechanisms telescope. Rotation of the distraction plates as they bear against bone, for instance the femoral condyles, potentially represents a source of friction which is avoided for the distractor of FIGS. 6 to 8. Additionally, for the embodiments of FIGS. 2 to 5 which have a knurled rim around the distraction plates, rotation of the distraction plates potentially could cause damage to surrounding soft tissue. This is avoided by arranging for non-rotating distraction plates.

The distractor of the fourth embodiment is driven, as is the case for the second and third embodiments, but differs in that it is driven from the anterior side (when the distractor is inserted in a knee joint). That is, rotation of the drive shaft 326 is about an axis which is perpendicular to the direction of motion of the distractor plates 304. This advantageously makes it easier to access the drive mechanism. The drive mechanism may be further adjusted to be driven from the anterior-medial or anterior-lateral sides in further embodiments of the invention to make it easier still for the surgeon to adjust the height of the distractor when it is positioned in the knee joint.

The drive mechanism for the fourth embodiment is based upon worm gears 350 contained within a central block 352. Central block 352 may be approximately 10 mm tall and arranged to be received within the intercondylar gap. The distraction mechanisms may have an expansion range between 4 mm and 10 mm. The worm gears 350 are coupled to shafts 354 which extend through bores 356 within the central block 352 and terminate at spur gears 358 external to the central block 352. Similarly to the second and third embodiments of the present invention, the gears 358 are driven by a splined shaft 332 at the end of the drive shaft 326. The tip 328 of the drive shaft 326 is cylindrical and arranged to be received within an axle hole 330 such that the splined shaft drives one or both of the gears 358 according to the axle hole 330 in which the drive shaft tip 328 is inserted. It will be appreciated that the drive mechanism may be modified so that the gears 358 do not protrude from the central block 352. In order to allow both distraction mechanisms to be driven simultaneously and in the same direction when the drive shaft tip 328 is inserted into the central axle hole 330 it is necessary to ensure either that the worm gears 350 have oppositely handed threads or that the distraction screw threads 316, 320a, 320b, 318a, 318b are oppositely handed for each distraction mechanism. As a further alternative the worm gears 350 may be removed and the distraction mechanisms directly driven by a drive shaft having a worm gear tip inserted into bores 356.

For the embodiments of FIGS. 1 to 5 the distraction plates 4, 104, 204 are free to rotate. Distraction is achieved by at least one intermediate stage 6, 106a, 106b, 206a, 206b rotating within a bore 8, 108, 208 formed directly within the base plate 2, 102, 202 causing the intermediate stages 6, 106a, 106b, 206a, 206b and the distraction plates 4, 104, 204 to telescope upwards. However, for the distractor of FIGS. 6 to 8 the distraction plates 304 are prevented from rotating relative to the base plate by tabs 360 which are received within a channel 362 in the central block 352. As the distraction plates 304 telescope upwards the tabs 360 slide upwards within channel 362. In order to allow distraction, rather than the intermediate stages 306a, 306b being directly coupled to the bore 308 they are coupled to a drive ring 364 which rotates within bore 308. Drive ring 364 comprises an internal screw thread 366 arranged to couple to the external screw threads 320a of the outer intermediate stage 106a.

The drive ring 364 is received within bore 308. The drive ring 364 is inserted from underneath the base plate 302 and an annular flange 380 rests against an upper lip 382 within the bore 308 to prevent the drive ring 364 passing out the top of the bore 308. The drive ring 364 is held in the bore 308 by three pins 384 which pass through pin holes 386 in the walls of the bore 308 and rest underneath the flange 380. Similarly to the embodiment of FIGS. 2 to 4, lock pins 370 are provided to limit the extent of travel of external screw threads 316, 320b and 320a to prevent the distraction mechanisms from disassembling themselves when collapsed or fully distracted.

Drive ring 364 further comprises an external gear 372 extending around its upper edge, which is arranged to be driven by the worm gear 350. As drive shaft 326 is turned, with its tip 328 inserted into an axle hole 330, the splined shaft 332 drives gear 358 and hence drives worm gear 350. Worm gear 350 engages the external gear 372 causing drive ring 364 to rotate within bore 30, but without causing the drive ring 364 to rise or fall. Given that the distraction plate 304 is prevented from rotating, the rotation of drive ring 364 causes telescopic movement between the distraction plate 304, intermediate stages 306a, 306b and the ring drive 364.

It will be appreciated that further modifications may be made to the distraction mechanism, while continuing to fall within the scope of the claims. For instance, in place of the intermediate stages being received within a bore in the base plate, they may extend around a post mounted on the base plate. Advantageously this would remove the possibility of the intermediate stages disassembling upon collapsing the distractor; however the minimum thickness of the distractor would be increased.

While embodiments of the present invention described above relate to a distractor for use in a knee replacement procedure, it will be appreciated that the invention is more generally applicable. It is a common requirement within orthopaedic surgery to distract bones to create or maintain a space within a joint, or to assess or measure a joint space. It will be appreciated that for differing applications the form of the distractor may vary. For instance, there may be only a single distraction mechanism or there may be more than two.

The distraction mechanisms may vary in size, and there may be a different number of stages. The distractor may be modified to couple to other instruments or prostheses. For the example of a knee joint distractor, the underside of the base plate may be modified to couple to a tibial tray or a force sensor. There may be an indicator on the distractor plates to show the distraction height. Advantageously the scale is amplified due to the rotary movement compared with the actual size of the displacement. There may be a bearing plate on the distraction plate so that while the distraction plate rotates the bearing plate freely spins to stop the rotating plate rubbing against bone. The size and shape of the base plate may vary according to the required application, for instance the size of the tibial tray to which the distractor is required to couple.

There may be detents or dents formed in the screw profiles so that as the mechanism rotates it "clunks" into position at predetermined distraction increments, for instance every 1 mm. Specifically, the exterior screw threads could comprises one or more detents and the internal screw threads could comprise one or more corresponding recesses, or vice versa. Advantageously, this would provide the surgeon with tactile feedback when the size of the distraction has increased by a predetermined increment, for instance 1 mm. This tactile feedback may be in addition to visual confirmation of the distraction size via a gauge on the outer periphery of the distraction plate.

Figure 9:
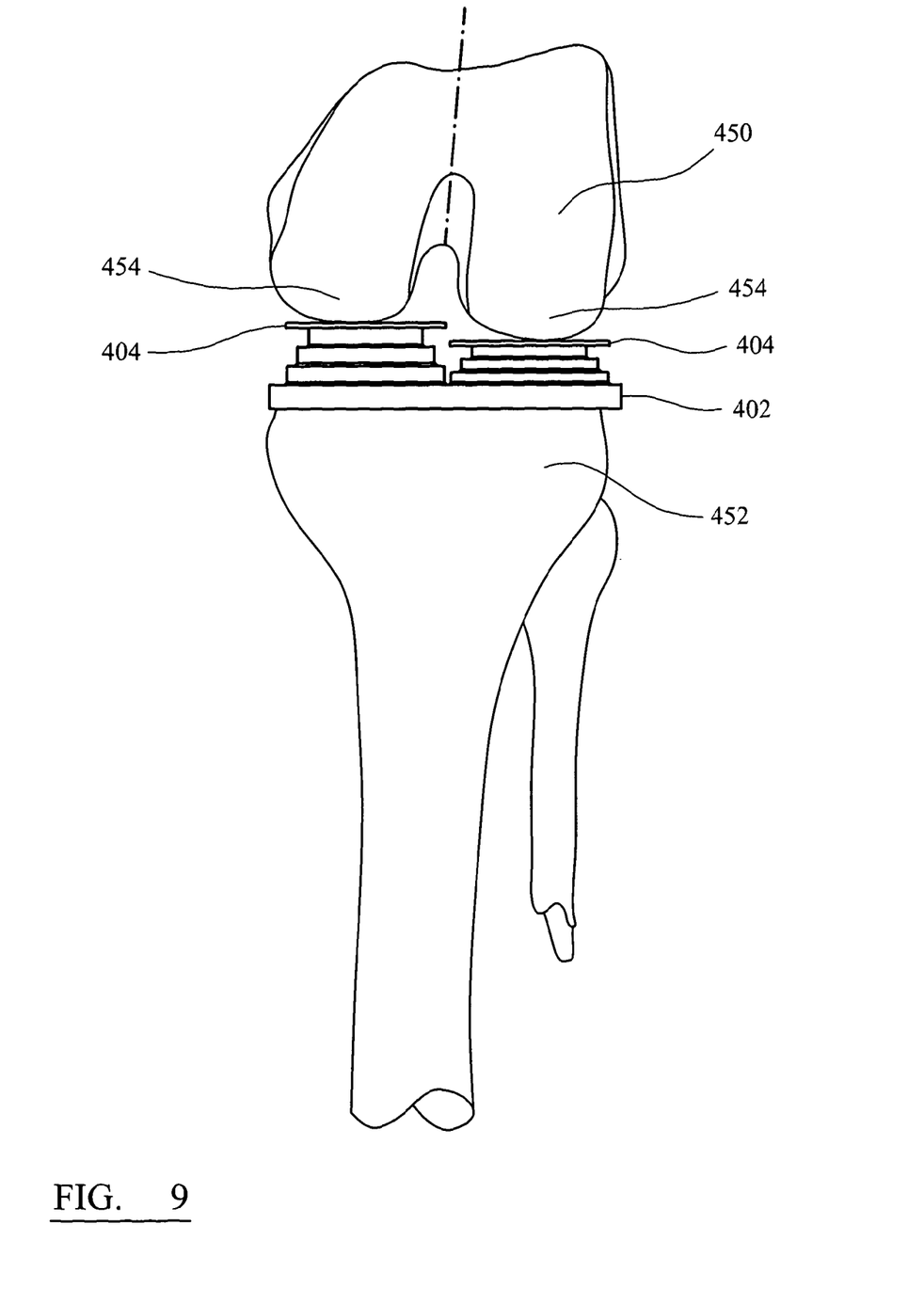
FIG. 9 illustrates an anterior view of a knee joint in flexion with a surgical distractor in accordance with an embodiment of the present invention distracting a gap between the femur and the tibia.

A method of using a distractor in accordance with an embodiment of the present invention will now be briefly described in connection with FIG. 9. A joint space, for instance between the femur and the tibia in a knee joint, must first be exposed and opened, for instance using laminar spreaders. A distractor can then be inserted. FIG. 9 illustrates a distractor in accordance with an embodiment of the present invention positioned between a femur 450 and a tibia 452. The knee joint is illustrated in flexion. The base plate 450 sits upon the proximal end of the tibia 452, which has been resected to provide a stable platform for the distractor. The femoral condyles, specifically when in flexion as illustrated in FIG. 9 the posterior condyles 454, bear against respective distraction plates 404. The distraction mechanisms are then driven individually or in tandem to distract the femur 450 and the tibia 452. In the view of FIG. 9 the left hand distraction mechanism is fully distracted and the right hand distraction mechanism partially distracted to create an uneven joint space. It can be seen that the effect of the uneven distraction is to cause external rotation of the tibia 452 relative to the femur 450. At each stage of distraction the size of the joint space and the tension in soft tissues surrounding the joint and movement of the joint may be assessed. When the joint space and the functioning of the joint are optimised the final amount of distraction may be recorded and used to select the required prosthetic components, for instance the thickness of tibial insert.

It will be readily apparent to the appropriately skilled person that further modifications may be made to the present invention and further applications may be found for the present invention from the teaching herein, without departing from the scope of the appended claims.

The invention claimed is:

1. A surgical distractor, comprising:
a base plate having an annular portion;
an intermediate stage comprising a ring coupled to the annular portion by a first coupling, the first coupling comprising three helical structures adapted such that the annular portion and the intermediate stage are coupled together at three points spaced apart around the circumference of the annular portion and the intermediate stage; and
a distraction plate having a circular portion, the circular portion being coupled to the intermediate stage by a second coupling, the second comprising three helical structures adapted such that the intermediate stage and the distraction plate are coupled together at three points spaced apart around the circumference of the intermediate stage and the circular portion of the distraction plate;
wherein the at least one of the helical structures of the first and second couplings are configured to adapt relative rotary movement between the intermediate stage and at least one of the base plate and the distraction plate about an axis of rotation into relative linear movement between the intermediate stage and the base plate or distraction plate along the axis of rotation; and
wherein the pitch of each helical structure for each of the first coupling and the second coupling are the same.

2. A surgical distractor, comprising:
a base plate having an annular portion;
an intermediate stage comprising a ring coupled to the annular portion by a first coupling, the first coupling comprising three helical structures adapted such that the annular portion and the intermediate stage are coupled together at three points spaced apart around the circumference of the annular portion and the intermediate stage;
a distraction plate having a circular portion, the circular portion being coupled to the intermediate stage by a second coupling, the second comprising three helical structures adapted such that the intermediate stage and the distraction plate are coupled together at three points spaced apart around the circumference of the intermediate stage and the circular portion of the distraction plate; and
a second intermediate stage coupled between the intermediate stage and the distraction plate
wherein the at least one of the helical structures of the first and second couplings are configured to adapt relative rotary movement between the intermediate stage and at least one of the base plate and the distraction plate about an axis of rotation into relative linear movement between the intermediate stage and the base plate or distraction plate along the axis of rotation.

3. A surgical distractor, comprising:
a base plate having an annular portion;
an intermediate stage comprising a ring coupled to the annular portion by a first coupling, the first coupling comprising three helical structures adapted such that the annular portion and the intermediate stage are coupled together at three points spaced apart around the circumference of the annular portion and the intermediate stage; and
a distraction plate having a circular portion, the circular portion being coupled to the intermediate stage by a second coupling, the second comprising three helical structures adapted such that the intermediate stage and the distraction plate are coupled together at three points spaced apart around the circumference of the intermediate stage and the circular portion of the distraction plate;
wherein the at least one of the helical structures of the first and second couplings are configured to adapt relative rotary movement between the intermediate stage and at least one of the base plate and the distraction plate about an axis of rotation into relative linear movement between the intermediate stage and the base plate or distraction plate along the axis of rotation; and
wherein each of the first coupling and the second coupling includes at least one inclined slot formed in at least one of the base plate, the intermediate stage and the distraction plate and at least one pin extending at least one of the base plate, the intermediate stage and the distraction plate sized and adapted to be received within the at least one inclined slot.

4. A surgical distractor, comprising:
a base plate having an annular portion;
an intermediate stage comprising a ring coupled to the annular portion by a first coupling, the first coupling comprising three helical structures adapted such that the annular portion and the intermediate stage are coupled together at three points spaced apart around the circumference of the annular portion and the intermediate stage; and a distraction plate having a circular portion, the circular portion being coupled to the intermediate stage by a second coupling, the second comprising three helical structures adapted such that the intermediate stage and the distraction plate are coupled together at three points spaced apart around the circumference of the intermediate stage and the circular portion of the distraction plate;

wherein the at least one of the helical structures of the first and second couplings are configured to adapt relative rotary movement between the intermediate stage and at least one of the base plate and the distraction plate about an axis of rotation into relative linear movement between the intermediate stage and the base plate or distraction plate along the axis of rotation; and wherein the distraction plate is arranged to rotate relative to the base plate to cause telescopic movement.

5. A surgical instrument kit comprising:

a surgical distractor comprising a base plate, an intermediate stage and a distraction plate, the base plate having an annular portion;

the intermediate stage comprising a ring coupled to the annular portion by a first coupling, the first coupling comprising three helical structures adapted such that the annular portion and the intermediate stage are coupled together at three points spaced apart around the circumference of the annular portion and the intermediate stage; and the distraction plate having a circular portion, the circular portion being coupled to the intermediate stage by a second coupling, the second comprising three helical structures adapted such that the intermediate stage and the distraction plate are coupled together at three points spaced apart around the circumference of the intermediate stage and the circular portion of the distraction plate;

wherein the at least one of the helical structures of the first and second couplings are configured to adapt relative rotary movement between the intermediate stage and at least one of the base plate and the distraction plate about an axis of rotation into relative linear movement between the intermediate stage and the base plate or distraction plate along the axis of rotation;

wherein the distraction plate comprises a knurled rim and the surgical distractor further comprises an axle hole formed in the base plate; and an adjustment drive shaft having a tip to be received within the axle hole and a splined shaft proximal to the tip arranged to engage the knurled rim of the distraction plate when the tip is inserted into the axle hole;

wherein rotating the drive shaft when the tip is received within the axle hole rotates the distraction plate relative to the base plate causing the distraction plate to move towards or away from the base plate.

6. The surgical instrument kit of claim 5, further comprising a drive ring received within a bore formed in the base plate and arranged to rotate within the bore without causing axial movement of the drive ring, wherein an intermediate stage is received within the drive ring and arranged to rotate within the drive ring bore such that the intermediate stage moves towards or away from the base plate.

7. The surgical instrument kit of claim 6, wherein the drive ring is arranged to rotate relative to the base plate while the distraction plate remains in a fixed angular position relative to the base plate to cause telescopic movement.

8. The surgical instrument of claim 7, wherein the distraction plate is prevented from rotating relative to the base plate by a locking tab engaging a channel within the base plate.

9. The surgical instrument of claim 7, wherein the drive ring comprises a gear ring and the surgical distractor further comprises a worm gear extending through a bore within the base plate and engaging the gear ring such that rotating the worm gear about a first axis causes the drive ring to rotate about a second axis transverse to the first axis; and an adjustment drive shaft arranged to engage the worm gear such that rotating the drive shaft causes the drive ring to rotate relative to the base plate and the distraction plate to move towards or away from the base plate.

10. The surgical instrument of claim 9, wherein the worm gear is connected to a rod having a spur gear at an opposite end, the surgical distractor further comprises an axle hole formed in the base plate; wherein the drive shaft has a tip to be received within the axle hole and a splined shaft proximal to the tip arranged to engage the spur gear when the tip is inserted into the axle hole; and wherein rotating the drive shaft when the tip is received within the axle hole rotates the spur gear causing the drive ring to rotate relative to the base plate and the distraction plate to move towards or away from the base plate.

* * * * *